United States Patent [19]
Dustin et al.

[11] Patent Number: 5,190,859
[45] Date of Patent: Mar. 2, 1993

[54] PURIFICATION OF LFA-3

[75] Inventors: Michael Dustin, Boston; Timothy Springer, Chestnut Hill, both of Mass.

[73] Assignee: Dana-Farber Cancer Institute, Inc., Boston, Mass.

[21] Appl. No.: 421,292

[22] Filed: Oct. 3, 1989

Related U.S. Application Data

[63] Continuation of Ser. No. 19,010, Feb. 26, 1987, abandoned.

[51] Int. Cl.$^5$ .................. C07K 3/18; C07K 15/14; G01V 33/566
[52] U.S. Cl. ........................ 435/7.24; 435/2; 435/7.8; 435/30; 435/243; 436/503; 436/543; 436/824; 530/395; 530/413; 530/806
[58] Field of Search ............ 435/7, 7.24, 2, 7.8, 435/30, 243; 436/543, 824, 503; 530/395, 413, 806, 810; 935/108

[56] References Cited

U.S. PATENT DOCUMENTS

| | | | |
|---|---|---|---|
| 4,169,090 | 9/1979 | Murray | 530/370 |
| 4,443,427 | 4/1984 | Reinherz et al. | 436/548 |
| 4,578,269 | 3/1986 | Morein | 424/88 |
| 4,956,281 | 9/1990 | Wallner et al. | 435/69.3 |

FOREIGN PATENT DOCUMENTS 8303678 10/1983 World Int. Prop. O. .

OTHER PUBLICATIONS

Kürzinger et al., *Journ. Biol. Chem.*, 257, 12412–12418, 1982.
Davies, In Weir (Ed.) *Handbook of Experimental Immunology*, 3rd ed., Blackwell Scientific Publications, Oxford, 1978, pp. 4.1–4.16.
Plunkett et al., J. of Immun., "Purification and characterization of the lymphocyte function–associated-2 (LFA-2) molecule", vol. 136, No. 11, pp. 4181–4187, (Jun. 1, 1986).
Barbosa et al., J. of Immun., "The mapping and somatic cell hybrid analysis of the role of human lymphocyte function-associated antigen-3 (LFA-3) in CTL-target cell interactions", vol. 136 No. 8, pp. 3085–3091, (Apr. 15, 1986).
Wolf et al., Clin. Research, "Monoclonal antibodies to T11, LFA-2, and LFA-3 antigens inhibit binding of human thymotcytes to autologous thymic epithelial cells", vol. 34 No. 2, p. 674A (Apr. 1986).
Krensky et al. *Hybridoma Technology in the Biosciences and Medicine*, "Human cytolytic T-lymphocyte clones and their function–associated cell surface molecules", Chapter 35, pp. 559–573, copyright 1985.
Gromkowski et al., J. of Immun., "Functional distinctions between the LFA-1, LFA-2, and LFA-3 membrane proteins on human CTL are revealed with trypsin pretreated target cells", vol. 134, No. 1, pp. 244–249 (Jan. 1985).
Krensky et al., J. of Immun., "LFA-1, LFA-2, and LFA-3 antigens are involved in CTL-target conjugations", vol. 132, No. 2, pp. 2180–2812 (Aug. 1983).
Krensky et al., J. of Immun., "The functional significance, distribution, and structure of LFA-1, LFA-2, and LFA-3: surface antigens associated with CTL-target interactions", vol. 131, No. 2, pp. 611–614, Aug. 1983.
Hildreth et al., Eur. J. of Immun., "A Human lymphocyte-associated antigen involved in cell-mediated lympholysis", vol. 13, pp. 202–207 (1983).
Sanchez-Madrid, Proc. Natl. Acad. Sci., "Three distinct antigens associated with human T-lymphocyte-mediated cytolysis: LFA-1, LFA-2, and LFA-3", vol. 79, pp. 7489–7493 (Dec. 1982).
Dustin et al., Journal of Experimental Medicine 165:677–692 (1987).
Hammarstrom, Scand. J. Immunol., 2:53–56 (1973).
Martin, J. of Immun. 131:180–185 (1983).
Dustin et al., Chemical Abstracts 110:152360b (24th of Apr., 1989).
Dustin et al., Chemical Abstracts 106:154407g (11th of May, 1987).
Shaw, Nature 323:262, 1986.

*Primary Examiner*—David Saunders
*Attorney, Agent, or Firm*—Fish & Richardson

[57] ABSTRACT

A method of purifying LFA-3 using affinity chromatography. Purified LFA-3 is useful for quantitating or separating out CD-2-containing cells.

12 Claims, 1 Drawing Sheet

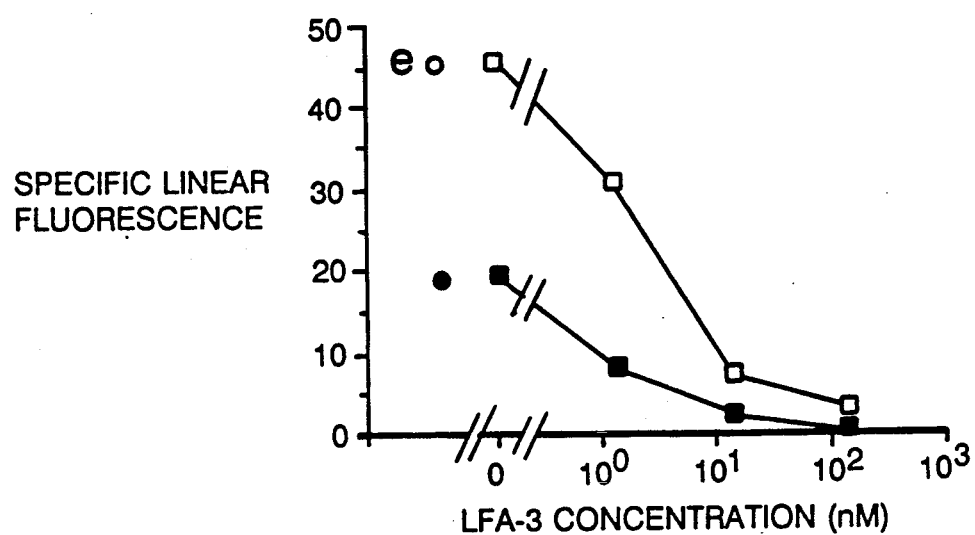
FIGURE

PURIFICATION OF LFA-3

This is a continuation of copending application Ser. No. 07/019,010 filed on Feb. 26, 1987, now abandoned.

BACKGROUND OF THE INVENTION

This invention was made in the course of work supported by governmental financing, and the government therefore has certain rights in the invention. Specifically, the work was supported by N.I.H. grant CA 31798.

This invention relates to T-lymphocyte responses.

Antigen-specific T-lymphocyte-mediated killing is a multistep process involving antigen recognition by a cytolytic T lymphocyte (CTL), adhesion of the CTL to a target cell, delivery of a lethal hit, and target cell lysis. Bystander cells and the CTL itself are unharmed in the killing reaction, and the CTL can detach and engage in further killing encounters. The response of Helper T lymphocytes to antigen, which is critical for the initiation of the immune response to many agents, is also dependent on adhesion of T lymphocytes to antigen presenting cells. Helper T lymphocyte responses are assayed by proliferation of lymphocytes or 1L-2 production.

The molecular basis of CTL-mediated killing and Helper T lymphocyte responses has been studied by preparing monoclonal antibodies (MAb) to both CTLs and their targets and selecting for those which block the killing response. Monoclonal antibodies to LFA-1 (LFA stands for lymphocyte function associated), CD2 (also called LFA-2, T11, or E-rosette receptor), and LFA-3 antigen molecules inhibit killing (Sanchez-Madrid et al., 79 Proc. Nat. Acad. Sci. 7489, 1982) and also inhibit Helper T lymphocyte dependent responses.

Human LFA-3 is a cell surface glycoprotein expressed on almost all human cells, which has a mean molecular weight of about 60,000 (Id.). It is immunoprecipitated by specific MAbs. LFA-3 is a found on target cells and antigen presenting cells, and killing of a target cell by an effector CTL or recognition of antigen presenting cells by Helper T lymphocytes is blocked by binding of LFA-3 MAb to the target cell or antigen presenting cells. Specifically, LFA-3 is found on monocytes, granulocytes, CTL's, B-lymphoblastoid cell lines, platelets, thymic epithelial cells, vascular endothelial cells, smooth muscle and fibroblasts (Krensky et al., Human cytolytic T-lymphocyte clones and their function-associated cell surface molecules, In Hybridoma technology in the biosciences and medicine, eds. Springer et al., Plenum Press, New York, 1985.

SUMMARY OF THE INVENTION

In one aspect, the invention features a method for purifying LFA-3 comprising contacting a liquid containing LFA-3 with an affinity column comprising anti-LFA-3 antibody to bind the LFA-3 to the LFA-3 antibody, and then eluting the LFA-3 from the affinity column using an acidic buffer.

In preferred embodiments the method further comprises passing the LFA-3 containing liquid through a column containing an irrelevant antibody, prior to contacting the liquid with the affinity column, in order to remove nonspecifically-binding proteins other than LFA-3; washing the affinity column, prior to the eluting step, with a buffer of a pH at which non-LFA-3 proteins are removed and LFA-3 is retained, most preferably the buffer has a pH between 10 and 11; the acidic buffer preferably has a pH between 2.5 and 4.0; the LFA-3 is purified from mammalian erythrocytes, monocytes, granulocytes, CTLs, B-lymphoblastoid cell lines, platelets, vascular endothelial cells, smooth muscle or fibroblasts or other cells expressing LFA-3 genes; the anti-LFA-3 antibody is monoclonal; the LFA-3 is solubilized by a detergent or phospholipase, such as phosphatidylinositol phospholipase C, prior to passing the liquid containing LFA-3 through the affinity column; preferably the detergent is non-ionic; and the irrelevant antibody is IgG.

In a second aspect, the invention features a method of detecting cells bearing a CD-2 antigen, the method comprising detecting binding of LFA-3 to the cells.

In a third aspect, the invention features a method of separating cells bearing CD-2 antigen from other cells in a mixture, the method comprising contacting the mixture with a solid support comprising LFA-3 to bind CD-2 bearing cells thereto.

In a fourth aspect, the invention features substantially pure biologically active LFA-3.

In a fifth aspect the LFA-3 may be used as a therapeutic agent to block or augment the immune response.

The diagnostic and therapeutic methods of the invention flow from our discovery that the specific role of LFA-3 in T lymphocyte adhesion is to act as a ligand for the T lymphocyte surface molecule CD2. CD2 is a glycoprotein of 50,000M, which is expressed on all T lymphocytes, thymocytes and a population of large granular lymphocytes which include cells with natural killer activity. CD2 is expressed early in the differentiation of T lymphocytes before they enter the thymus. Combinations of MAb to CD2 induce proliferation and function of T lymphocytes, thymocytes and natural killer cells. Therefore we propose that the biological ligand of CD2, is LFA-3, can have similar effects.

LFA-3 and CD2 is the first pair of antigens, on a target cell and CTL, respectively, to be identified as a binding pair. That is, the two antigens interact to allow recognition of the two cell types. Blocking of either of these antigens by a MAb prevents this cellular interaction. Our discovery of the role of LFA-3, together with our new purification method, which will provide LFA-3 in quantity, allows detection of CTLs and other cells having CD2 molecules on their cell surface, and also allows specific blocking of the CD2 molecule by the purified LFA-3 without use of an antibody. Since LFA-3 is a natural component of the human body it can be introduced into humans without eliciting immune responses. In contrast MAb's which are produced in non-human species stimulate the production of antibodies and are neutralized. LFA-3 is broadly distributed and may have a general role in T lymphocyte adhesion and the recirculation, extravascular migration, and development of T lymphocytes.

Other features and advantages of the invention will be apparent from the following description of the preferred embodiments thereof, and from the claims.

DESCRIPTION OF THE PREFERRED EMBODIMENTS

The drawing will first briefly be described.

DRAWING

The FIGURE is a graphical representation of the activity of purified LFA-3. Purified LFA-3 binds to CD2 on T-lymphocytes, as shown by inhibition of CD2 MAb binding.

METHODS

Many of the methods used below are described in detail in Plunkett et al., (136 J. Immunol. 4181, 1986) and Sanchez-Madrid, supra.

In general, LFA-3 is purified, according to the invention, by passage over an affinity column. We have found that LFA-3 forms an unusually stable complex with monoclonal antibodies to LFA-3, even at an alkaline pH. This permits purification, in a single step, of biologically active LFA-3.

We have also found that human erythrocytes contain large amounts of LFA-3 antigen and can be used as a source for its purification. They are the richest source of human material readily available at reasonable cost. Fresh human erythrocytes have about 5,000 LFA-3 sites per cell. This is much less than the number of LFA-3 molecules on B lymphoblastoid cell lines (about 200,000), but a unit of outdated red blood cell contains about 250 μg of LFA-3 based on this site number estimate. Of course, if the appropriate cell lines are available, LFA-3 can be extracted and purified from them in a similar manner to that described below for erythrocytes.

LFA-3 is associated with the erythrocyte membrane by a hydrophobic domain and must be solubilized using detergents. Preferably a mild, non-denaturing detergent (e.g., Triton X-100) is used since it does not denature the protein. Alternatively, since LFA-3 is attached to cells with a glycolipid anchor, it can be solubilized with phosphatidylinositol phospholipase C without need for detergents. In general, erythrocytes are lysed at less than or equal to 50% of the packed volume with buffered detergent or phospholipase solution at neutral pH for about 60 min., below 4° C. Protease inhibitors are used to prevent degradation of LFA-3. The lysed erythrocytes are then centrifuged at high speed, to remove insoluble material, and the supernatant (lysate) saved for chromatography.

Affinity chromatrography is performed by passing the lysate through an affinity column composed of anti-LFA-3 monoclonal antibody coupled to an inert matrix, at about 2-20 mg anti-LFA-3/ml. The lysate is preferably first passed through a column containing inert matrix having a bound irrelevant antibody (i.e., one which does not bind LFA-3) to adsorb non-specifically binding substances, and then through the column with anti-LFA-3 MAb. (At 2mg MAb/ml this column can bind all the LFA-3 from 1 liter of lysate.) The column is then washed with several volumes of neutral pH buffer containing, for example, 0.15M salt (NaCl or KCl), and a non-ionic detergent. (The detergent may be left out of the washes and elution buffer, but the yield of LFA-3 may be decreased.)

In general, for purification and then elution of LFA-3, the column is washed with an alkaline pH buffer (pH 10-11) and then neutralized. Material eluting from the alkaline washes is saved and neutralized, since it contains some LFA-3 which can be recovered later. The alkaline pH wash removes almost all contaminating proteins from the column. This is a critical step since the purification is based on the unusually high stability of the LFA-3-MAb complex at alkaline pH. LFA-3 is eluted from the column with acidic pH buffer (pH 2.5-4) at a slow flow rate. LFA-3 elutes in less than about one column volume and is neutralized immediately. (The column is also neutralized and can be reused many times.) LFA-3 in the fraction is determined by the binding of $^{125}I$ anti-LFA-3 MAb to nitrocellulose paper with a small amount of each fraction bound (Dot blot assay, Plunkett, supra, 119 Hawkes et al., Anal. Biochem. 142, 1982).

The following is an example of a method of purifying LFA-3. Those skilled in the art will realize that this invention is not limited to the exact conditions used in this example but that the antibodies, buffers, columns and environmental factors can readily be changed, within the spirit of the invention.

EXAMPLE

Purification of LFA-3 Using TS2/9 MAb

The mouse anti-human MAb TS2/9 (anti-LFA-3, IgG1, Sanchez-Madrid, supra) was used as purified IgG or as dilutions of culture supernatants. Briefly, anti-LFA-3 was prepared by injecting BALB/c mice with cells from the HLA-DR CTL line, fusing spleen cells from those mice with P3X63Ag8.653 or NSI and growing the hybridoma cultures which showed greater than 30% inhibition of killing of target cells by CTLS. One hybridoma produced antibodies against LFA-3. Other Mab's to LFA-3 can be made by immunizing mice with LFA-3 and isolating anti-LFA-3-producing hybridoma clones, all by conventional methods. Monoclonal antibodies are selected for those which inhibit killing by CTL cell lines by binding to the target cells, and which precipitate a protein of 60-70,000 Molecular weight. TS2/9 MAb was purified by standard procedures (Id.) from hybridoma culture supernatants by $(NH_4)_2SO_4$ precipitation and protein A affinity chromatography.

Purified IgG was coupled to Sepharose CL-4B by a modification of the method of March et al. (60 Anal. Biochem. 149, 1974). Briefly, washed Sepharose CL-4B (Pharmacia, Upsala, Sweden) was activated with 40 mg/ml CNBr in 1M $Na_2CO_3$ for 10 min. on ice and then washed with distilled water and 0.1 mM HCl. The activated Sepharose was filtered to a moist cake and added to purified antibody solution with 2-4 mg/ml IgG (TS2/9 or mouse IgG) in 0.05M NaCl and 0.1M $NaHCO_3$, pH 8.4. The suspension was mixed end over end for 20 hr and any remaining reactive groups blocked by addition of ethanolamine to 50 mM and incubation for 1 h. The supernatant was checked for antibody by measuring absorbance at 280 nm. Coupling was usually in the order of 90%. The Sepharose was poured into a column and washed with one cycle of pH 11 and pH 3 buffers (see below) before use for affinity chromatography.

LFA-3 was purified in Triton X-100 micelles by affinity chromatography. All operations were done at 4° C. Outdated human erythrocytes were obtained from the American Red Cross (Needham, Mass.). Cells from 2 units of whole blood were washed 3 times with phosphate buffered saline (PBS), and the packed cells pelleted to about 500 ml. Another 500 ml of PBS with 2% Triton X-100, 1 mM phenylmethylsulfonyl fluoride, 5 mM iodoacetamide and 150 mTIU/ml aprotinin was added to the red cell suspension while stirring. After 1 h the lysate was centrifuged at 150,000 g for 2 h, and the cleared lysate passed over the two antibody columns in series, at a flow rate of 20 ml/hr.

The first column contained mouse IgG CNBr Sepharose CL-4B (2 ml at 2 mg/ml) to absorb contaminants and filter out particulate material. The second column was TS2/9 MAb CNBr Sepharose CL-4B column (5-10 ml at 2 mg/ml). After passage, the second column was washed with 5 column volumes of 50 mM sodium phosphate pH 7.2, 0.025M NaCl, 0.1% Triton X-100, 5 column volumes of 20 mM triethylamine pH 11, 0.25M NaCl, 0.1% Triton X-100 and 2 column volumes of the phosphate buffer, all at a flow rate of 1 ml/min. The remaining bound LFA-3 was then eluted with 5 column volumes of 50 mM glycine pH 3, 0.25M NaCl, 0.1% Triton X-100 at a flow rate of 20 ml/hr. LFA-3 generally eluted in 1 column volume and was neutralized by collection into 0.1 vol of 1M tris pH 8.6, 0.1% Triton X-100. LFA-3 purification was followed in a semiquantitative manner using a "dot blot" assay with $^{125}$I-TS2/9 MAb.

The affinity purification strategy described above takes advantage of the unusual stability of the LFA-3 MAb complex to alkaline pH (pH 11) which elutes many proteins from affinity columns. This high pH also has the effect of solubilizing many contaminating proteins from the column matrix and probably breaks persistent interaction of contaminants with LFA-3. This wash step allows purification of homogeneous pure LFA-3 from the affinity column in a one step isolation procedure. Sometimes a small amount of hemoglobin (less than 10%) is eluted at pH 3 with LFA-3, but this is readily removed by a second passage over the same affinity column, as desired. The purified LFA-3 from erythrocytes migrates on SDS-PAGE as a broad band of $40,000-70,000M_r$. This is lower in molecular weight than LFA-3 from B lymphoblastoid cells but is similar to LFA-3 from an epitheliod carcinoma.

Activity of Purified LFA-3

Soluble LFA-3

Purified LFA-3 binds to the CD2 molecule on T lymphocytes and can inhibit the interaction of CD2 with cell surface LFA-3. The FIGURE shows the ability of different concentrations of LFA-3 to inhibit the binding of anti-CD2 MAb. This data indicates that soluble LFA-3 can bind directly to CD2 and saturates CD2 at a concentration of about 140 nM.

Referring to the FIGURE, the ability of purified LFA-3 to interfere with anti-CD2 MAb binding was determined using flow microfluorometry, as follows. MAbs were titrated against Jurkat and peripheral blood lymphocytes to determine the lowest concentration of MAb giving optimal staining. The Jurkat T lymphoma cells (from Dr. M-K Ho, Dupont/NEN Boston, Mass.) and peripheral blood T cells were obtained by depleting adherent cells by twice incubating peripheral blood mononuclear cells in complete media (RPMI 1640 (Sanchez-Madrid, supra) containing 10% Fetal Bovine Serum (FBS)) in tissue culture treated petri dishes at $2 \times 10^7$ cells/10 cm plate for 60 min., and gently removing adherent cells; peripheral blood mononuclear cells were prepared by dextran sedimentation of whole blood and ficoll-hypaque (d=1.077, Sigma) centrifugation. All operations were carried out at 4° C. The cells ($10^5$) were incubated with LFA-3 or control buffer in 20 μl of HBSS 15% BSA containing Bovine serum albumin (BSA) for 60 min. MAb were added in an additional 20 μl of the same buffer and the suspension incubated 15 min. The cells were washed three times and incubated with fluorescent FITC goat anti-mouse IgG (H+L, Zymed, San Francisco, Calif.) for 30 min, washed three times, fixed with 1% paraformaldehyde and analyzed within one week on a Coulter epics V flow cytometer.

The above cells were incubated for 1 h on ice with either LFA-3, at the indicated concentration (open squares: Jurkat T cells; and closed squares: peripheral cells), control buffer of the same composition as the LFA-3 containing solution (the "0" LFA-3 point), or purified LFA-1 membrane protein (open and closed circles). After addition of anti-CD-2 MAb (Plunkett, supra) the cells were washed, incubated with the fluorescent goat anti-mouse IgG and analyzed to quantify binding of the MAbs. Non-binding and binding control MAb were used in all experiments to determine specific fluorescence and the specificity of the LFA-3 effect on anti-CD2 binding.

The results indicate that purified LFA-3 causes a dose dependent inhibition of anti-CD2 MAb binding and that LFA-3 probably saturates CD2 at less than 140 nM. A control membrane protein had no effect on anti-CD2 MAb binding and LFA-3 did not effect the binding of anti-LFA-1 MAb (prepared as described by Plunkett, supra) used as a control.

The table below shows that purified LFA-3 can inhibit the CD2 dependent interaction between human T lymphocytes and sheep erythrocytes. This is a convenient assay for the CD2 dependent adhesion pathway. Jurkat T lymphoblastoma cells ($10^5$) were mixed with sheep erythrocytes ($10^7$) in 10 μl of isotonic solution with 15% BSA to absorb detergent. Additions of MAb and/or purified LFA-3 were made in 10 μl of the same solution and the suspension was incubated on ice for 15 min, centrifuged for 5 min at 200 g, and after 1 h on ice the cells were gently resuspended, and scored for percent of nucleated cells with more than 3 erythrocytes adherent. The results indicate that anti-CD2 MAb inhibits this rosetting phenomena. (The rosetting is not inhibited by anti-LFA-3 since the LFA-3 homologue on sheep erythrocytes is not recognized by the anti-human-LFA-3 MAb.) Purified LFA-3 protein inhibits this rosetting completely and anti-LFA-3 MAb appears to neutralize the LFA-3 activity by combining with LFA-3 in solution.

|  | % SRBC rosettes | |
| --- | --- | --- |
|  | Jurkat T cell line | Peripheral blood lymphocytes |
| control | 80 | 30 |
| Anti-CD2 MAb | 0 | 0 |
| LFA-3 (70 nM) | 0 | 0 |
| Anti-LFA-3 MAb | 76 | 32 |
| LFA-3 + αLFA-3 MAb | 74 | 36 |
| LFA-1 (1000 nM) | 81 | 29 |

In another experiment, inhibition of LFA-3 binding to CD-2 containing cells by anti-LFA-3, was demonstrated. To label LFA-3, LFA-3 in Triton X-100 micelles was dialysed against borate buffered saline (pH 8.2), labelled with $^{125}$I using 1,3,4,6-tetrachloro-3a, 6-diphenylglycoluril (Iodogen; Peirce, Rockford, Ill.) according to the method of Fraker et al., (80 Bioc. Biop. Res. Comm. 1849, 1978), and then dialysed against PBS. The purity of the iodinated LFA-3 was greater than 80% by SDS-PAGE, and specific activity was estimated at 170 Ci/mmol. Binding assays were done on $2 \times 10^6$ cells in 100 μl with an input of 80,000 cpm in HBSS, containing 3% BSA. After 60 min at 4° C. the assay was terminated by centrifugation through a 0.8 ml 15% BSA cushion. The supernatant was thoroughly aspirated and the tip of the centrifuge tube containing the pellet was excised and counted. MAb was added 15 min prior to addition of the $^{125}$I LFA-3.

We found that iodinated LFA-3 bound to Jurkat cells and 80% of this binding was inhibitable by excess unlabelled LFA-3 and also by TS2/18 (a cell line having CD-2 antigen, Plunkett, supra).

Since the $^{125}$I LFA-3 was 80% pure and about 2% of input counts were bound in these experiments it was important to demonstrate that the "specific" binding was due to material bearing the TS2/9 epitope. Inclusion of TS2/9 and TS2/18 in the assays was no more potent at inhibiting binding than either alone, suggesting that both MAb were blocking binding of the same species. In addition, we found that iodinated LFA-3 bound to the SKW3 cell line (obtained from Dr. P. Cresswell, Duke University, Durham, N.C.) at a lower level than the other cell lines, corresponding to the lower level of CD2 expression on SKW3 compared to these cell lines.

Other flow microfluorometric experiments demonstrated that soluble LFA-3 interacts with the same site on CD2 as TS2/18 MAb. In addition we found that LFA-3 causes aggregation of Jurkat cells, and that this aggregation is inhibited by anti-CD2 MAb.

Membrane Associated LFA-3

LFA-3 normally functions as a protein anchored to the membrane by a hydrophobic domain. Therefore it is important to demonstrate that the purified protein can function in lipid bilayers.

LFA-3 was reconstituted into liposomes (artificial membranes) by octyl glucoside (OG) dialysis (Gay et al., 136 J. Immunol. 2026, 1986) and the liposomes fused onto glass coverslips to allow observation of cell binding. Briefly, LFA-3 was eluted from the affinity column in the presence of 34 mM (1%) OG instead of Triton X-100. Lipids in chloroform were mixed at a ratio of egg phosphatidylcholine:cholesterol of 7:2. The lipids (0.5 mg) were then dried under a nitrogen stream and placed under reduced pressure for 1 h to remove residual chloroform. The lipid film was taken up into 1 ml of protein solution with 20-30 ug of protein and 34 mM OG and dialysed against two changes of PBS and one of HBSS over 36-48 h. As a control, human glycophorin (Sigma) was also reconstituted using the same procedure.

In the following experiments Concanavalin cells (Con A blasts) were prepared by culturing peripheral blood mononuclear cells with 1 $\mu$g/ml Con A in RPM1-1640 20% FBS at $5\times10^5$ cells/ml for 3 days. The Con A was washed out and the cells grown in 1 ng/ml recombinant IL-2 for at least 3 days. These cells were labelled with $^{51}$Cr (by incubating $10^7$ cells with 300 $\mu$Ci of Na $^{50}$CrO$_4$ in 3 ml for 90 min) to allow quantification, and washed with methyl-$\alpha$-D-mannopyranoside to remove any residual Con A from the cells surface.

Planar membranes were prepared according to Brian et al., 81 Proc. Natl. Acad. Sci. 6159, 1984. Briefly, round glass coverslips (11 mm) were boiled in 1:6 7X Limbro detergent water for 15 min. They were then washed extensively over 24 h with distilled water and then soaked overnight in 70% ethanol and allowed to dry. A drop (100 $\mu$l) of liposome suspension diluted to 0.1 to 0.2 mM lipid was placed in wells of 24 well cluster plates (Falcon). Glass coverslips were gently place on top of the lipid suspension drops and left for 20-30 min. at ambient temperature. The well was washed three times with assay media (RPMI 1640, 10% FBS, 25 mM Hepes) to remove unfused liposomes. The lipid surface was never exposed to air.

When Con A blasts were gently centrifuged onto the above described planar membranes and incubated at 37° C. for 15 min., or 4° C. for 1 h, greater than 90% of cells bound to the planar membranes expressing LFA-3, but not to those containing human glycophorin. Pretreatment of the Con A blasts with TS2/18 or pretreatment of the LFA-3 bearing planar bilayer with TS2/9 F(ab')$_2$ (the fragment of IgG without Fc) inhibited greater than 95% of the binding observed, essentially to the level of that seen with human glycophorin bearing planar membranes. When the LFA-3 bearing planar membrane was treated with TS2/9 and all unbound MAb washed out, inhibition of Con A blast binding was still greater than 90% demonstrating that the blocking effect of TS2/9 was due to binding to the planar bilayer, not the T lymphocytes. (The low level of binding observed to the control glycophorin planar membranes and to LFA-3 planar membranes in the presence of TS2/18 and TS2/9 is probably due to trapping of cells under the coverslip and perhaps incomplete removal of unbound cells.)

For an adhesion molecule, LFA-3 has an unexpectedly high affinity for cell binding. The predicted dissociation constants for most adhesion molecules, taking into account that they can interact with extremely high valency in mediating cell adhesion, appears to be in the order of 1 $\mu$M or greater. Our data indicate that LFA-3 binds to cells with a dissociation constant in the order of 10 nM.

It is clear that erythrocyte LFA-3 can act as a potent ligand for CD2, when present at the high density used in the above reconstitution experiments. Therefore, LFA-3 from erythrocytes appears functionally similar to the equivalent LFA-3 antigen from more classical target cells involved with T lymphocyte adhesion. The molecular weight of LFA-3 from erythrocytes is also similar to that of LFA-3 from the epithelioid cells, such as strain A431.

Use

Purified LFA-3, or LFA-3 incorporated into artifical membranes, can be used to detect T-cell subsets and cells bearing CD2 antigen, using standard techniques as described above, e.g., radioimmunoassay with $^{125}$I-LFA-3 or binding cells to LFA-3 in artificial membranes. Further, LFA-3 in artificial membranes can be bound to a solid support such as a coverslip, as described above, and used to separate B and T-cells. This will allow determination of the proportion of T-cells in a population, and is useful for clinical diagnoses and monitoring of diseases characterized by excess numbers of T-cells, e.g., autoimmune diseases, allograft rejections, and graft-versus-host disease. T-cells may be purified by this technique.

Purified LFA-3 can also be used to competitively inhibit reactivity of T-lymphocytes with other cells. A therapeutically effective amount of LFA-3 in a physiologically compatible buffer, such as saline, can be injected into a human patient (50–500 $\mu$g/kg of patient/day) to saturate CD2 receptor sites and thereby treat diseases characterized by excessively reactive T-cells, e.g., autoimmune diseases such as rheumatoid arthritis; allograft rejection; and graft-versus-host disease. In addition, monoclonal antibodies to purified LFA-3 of the invention can be used to block LFA-3 on target or presenting cells, and prevent some T-lymphocytes from interacting with them.

Other embodiments are within the following claims.

We claim

1. A method for purifying LFA-3 comprising contacting a liquid comprising LFA-3 with an affinity column comprising anti-LFA-3 antibody to bind LFA-3 to said anti-LFA-3 antibody, washing said column with a first alkaline buffer, and then eluting said LFA-3 from said affinity column using a second acidic buffer, to provide purified LFA-3 capable of binding to CD2 antigen on T-lymphocytes.

2. The method of claim 1, further comprising passing said LFA-3-containing liquid through a column containing an irrelevant antibody prior to contacting said liquid with said affinity column, to remove from said liquid non-specifically proteins other than LFA-3.

3. The method of claim 1 wherein said second buffer has a pH between 2.5 and 4.0.

4. The method of claim 1 wherein said LFA-3 is purified from mammalian erythrocytes, monocytes, granulocytes, CTLs, B-lymphoblastoid cell lines, myeloid cell lines, platelets, vascular endothelial cells, epithelial cells, smooth muscle, or fibroblasts.

5. The method of claim 1 wherein said anti-LFA-3 antibody is monoclonal.

6. The method of claim 1 wherein, prior to said step of contacting said liquid with said column, said LFA-3 is solubilized by a detergent or a phospholipase.

7. The method of claim 6 wherein said detergent is non-ionic.

8. The method of claim 2 wherein said irrelevant antibody is IgG.

9. The method of claim 1 wherein said first buffer has a pH between 10 and 11.

10. A method of detecting a cell bearing a CD2 antigen, said method comprising detecting binding of purified LFA-3 to a cell, said LFA-3 being capable of binding to CD2 antigen on T-lymphocytes, wherein said binding specifically indicates the presence of CD2 antigen on said cell.

11. A method of specifically separating cells bearing CD2 antigen from other cells in a mixture, said method comprising contacting a mixture of cells including CD2 antigen-bearing cells with a solid support comprising purified LFA-3 capable of binding to CD2 antigen on T-lymphocytes, to bind said CD2-antigen-bearing cells thereto.

12. Substantially pure LFA-3 capable of binding to CD2 antigen on T-lymphocytes.

* * * * *

UNITED STATES PATENT AND TRADEMARK OFFICE
CERTIFICATE OF CORRECTION

PATENT NO. : 5,190,859

DATED : March 2, 1993

INVENTOR(S) : Dustin et al.

It is certified that error appears in the above-indentified patent and that said Letters Patent is hereby corrected as shown below:

In column 9, line 19, insert --binding-- after "non-specifically".

Signed and Sealed this

Twelfth Day of September, 1995

Attest:

BRUCE LEHMAN

*Attesting Officer*     *Commissioner of Patents and Trademarks*